(12) United States Patent
Weyens et al.

(10) Patent No.: US 7,645,579 B2
(45) Date of Patent: Jan. 12, 2010

(54) T227-1 FLANKING SEQUENCE

(75) Inventors: Guy Weyens, Beersel (BE); Steve Barnes, Petit-Hallet (BE); Inge Rosquin, Koningshooikt (BE)

(73) Assignee: SES Europe N.V./S.A., Tienen (BE)

( * ) Notice: Subject to any disclaimer, the term of this patent is extended or adjusted under 35 U.S.C. 154(b) by 343 days.

(21) Appl. No.: 11/750,196

(22) Filed: May 17, 2007

(65) Prior Publication Data

US 2009/0265817 A1    Oct. 22, 2009

Related U.S. Application Data

(62) Division of application No. 10/415,602, filed as application No. PCT/GB01/05321 on Nov. 30, 2001, now Pat. No. 7,241,567.

(60) Provisional application No. 60/250,110, filed on Nov. 30, 2000.

(51) Int. Cl.
*C12Q 1/68* (2006.01)
(52) U.S. Cl. .................. 435/6; 435/91.1; 435/91.2; 536/23.1; 536/24.33
(58) Field of Classification Search .................. None
See application file for complete search history.

(56) References Cited

FOREIGN PATENT DOCUMENTS

| | | |
|---|---|---|
| EP | 0218571 B1 | 4/1987 |
| EP | 0221044 B1 | 5/1987 |
| EP | 1167531 A1 | 1/2002 |
| WO | 92/00449 A1 | 1/1992 |
| WO | 99/23232 A1 | 5/1999 |
| WO | 99/43838 A1 | 9/1999 |
| WO | 00/49179 A1 | 8/2000 |
| WO | 01/32919 A2 | 5/2001 |
| WO | 01/66799 A2 | 9/2001 |

OTHER PUBLICATIONS

Mannerlof, M., et al., "Transgenic Sugar Beet Tolerant to Glyphosate," Euphytica 94(1):83-91, 1997.

*Primary Examiner*—Heather G Calamita
(74) *Attorney, Agent, or Firm*—Christensen O'Connor Johnson Kindness PLLC

(57) ABSTRACT

A herbicide resistant transformed sugar beet that is detectable by the specific primers developed to match the DNA sequences that flank the left and/or right border region of the inserted transgenic DNA and the method of identifying primer pairs containing plant genomic DNA/plasmid DNA. More specifically, the present invention covers a specific glyphosate resistant sugar beet plant having an insertion of the transgenic material identified as the T227-1 event. The present invention additionally covers primer pairs: plant genomic DNA/Plasmid DNA that are herein identified. Additionally, these primer pairs for either the left or the right flanking regions make an event specific test for the T227-1 insert of transgenic material.

5 Claims, 12 Drawing Sheets

FIGURE 1: Transformation event T227-1 with positions of the specific primers

Diagrammatic interpretation of the Southern blot results.

Plasmid sequence at the right border.

FIGURE 4

Sequence of the right border breakpoint.

```
Sugarbeet         GGACAGGACA CGACAGCTCC TCACGAGGTA ATGGATATCA TTAGAGAAAG   50
genomic           AGCGGAACAA ATATTACTCA AATGGAGGAT TTATGAAAGT AATAGATATA  100
sequence          CTTTACTAGA AAAGGAAGAT TGTCATGATT CAACACCAAA TGACACTTAA  150
98K89 primer      ATTAAGAACC CACCCTCATCT TAAACCAAAC TAAAATATCA TTTAATACAT  200
                  ATCCAAGTCA TAATCTACTA GTAGTTTTGC TTGGTGAGAT TACATAAATAT 250
BglI restriction site   ATCACTAATA TATAAGAAAT TTATTTTTCA ATCA AGATCT ATACAACTAA  300
                  TAACTGAAGT AGGAGAAGAT ATGGGATTGG TGTGGGAAGAT GGCTTCATGT  350
Integrated plasmid   CCATGTGTTT ATTCCCATCA AGCTTGAGCT CAGGATTTAG CAGCATTCCA  400
sequence                         HindIII restriction site      RB12 primer
```

FIGURE 5

Alignment of the right breakpoint region and the untransformed plant allelic sequence.

UNTRANSF          ATTTAAATRTC
T227-1 right      AATTAAGAACCCACCTCTCATCTTAAACCAAACTAAAATATC UNTRANSF          VVKTTGMCACATATCCAAGTCATAATCTACKASYAGTTTKG
T227-1 right      ATTTAATACATATCCAAGTCATAATCTACTAGTAGTTTTG UNTRANSF          CTTGGTGAGATTACATAATAKATCACTAATATATAASAAAA
T227-1 right      CTTGGTGAGATTACATAATATATCACTAATATATATAAGAAA UNTRANSF          TTTATTTWTCAATCAAGATCTATACAACTAATWMCTGAAG
T227-1 right      TTTATTTTTCAATCAAGATCTATACAACTAATAACTGAAG UNTRANSF          TAGGAGAAGATATGGGATTGGTGTGTGGGASATGGATTCCCC
T227-1 right      TAGGAGAAGATATGGGATTGGTGTGTGGGAGATGGCTTCATG UNTRANSF          ATATAAAGTAAAGAGAGTCAA
T227-1 right      TCCATGTGTTTATTCCCATCAAGCTTGAGCTCAGGATTTA
                  17bp fragment    plasmid sequence Plasmid sequence at the left border.

FIGURE 7

Sequence of the left border breakpoint. (SEQ ID NO:10)

| | | | | | |
|---|---|---|---|---|---|
| AATGTNCTTT | CATTTTATAA | NAACGCTGCG | GACATCTACA | TTTTTGAATT | 50 |
| GANAAAAAAT | TGGTAATTAC | TCTTTCTTTT | TCTCCATATN | GACCATCATA | 100 |
| CTCATTGNTG | ATCCATGTAG | ATTTCCCGGA | CATGANGCCA | TTTCCCATAT | 150 |
| CTTCTCCTAC | TTCNAGTCNA | TTAGTTGTAT | AGATCTTGAT | TGAAAAATAA | 200 |
| ATATTTGTCC | CAACTCTCTT | TTATTCCCTG | TGTCCATGTC | TGAACAACTT | 250 |
| TCGAATTTTC | TTCCTAATAA | TCTCGCGATA | ACTTGCATGG | TTTGGAACAT | 300 |
| GCAATGAGCG | AGAAATANAA | ATTTTATTTC | TGCTTTGAAA | GCAATTGTTA | 350 |
| GAATGCATCG | TCCTACTGTG | ATTGCATGAG | TGGAAACACA | TATGGGAGGA | 400 |
| AATCAAGCTA | TGTCTATTGC | ATCTGCTCTG | GGGTACTCTG | GTCATACTCG | 450 |
| TGTCGATGCC | ATGGGTTTT | TAGGGGAAT | TTTGATTTAT | TGGAAACCAG | 500 |
| AATTGGTTAC | CATAGAACCT | ATCATTAGAC | ATGCATGATC | AACATATAAC | 550 |
| CATGGAAATA | AAAAGGGTAG | GGGCTATTCT | TTGGTATTTC | TCAGCGGTTT | 600 |
| ATGCGAGTCC | CGACCCTACA | AAACGCCAAG | TTCTTTGGCA | AGAATTAAGA | 650 |
| AATTTCGCTC | GAACTCATAA | TCAAGCTTGG | CTCATAGCAG | GAGATTTTAA | 700 |
| TGATACCAGA | TATTCCTATG | AAAGGAATAC | TGCTTGTTCG | GAAACTCAAC | 750 |
| GTTGTCTCTT | AGTTTCAATG | ATTGGGTNNN | TGACATGGAT | TAATGAA | 797 |

- Integrated Plasmid sequence
- LB8 primer
- *Bgl*II restriction site
- Sugarbeet genomic sequence
- *Hind*III restriction site
- 98K86 primer

FIGURE 8

Alignment of the left breakpoint region and the untransformed plant allelic sequence.

```
UNTRANSF         ATATGGGAT-TGGTGTGGGASATGGATTCCCCATAT
                 ** *  ** *  **  *  *  * **   **

T227-1 left   AAGCCATTTCCCATATCTTCTCCTACTTCNAGTCN----AT
              plasmid sequence       49bp fragment UNTRANSF         AAAGTAAAGAGAGTCAACAAGAAGAWATAAAATATTTGTCC
                 * * * *** * * * * ***** *******

T227-1 left    TAGTTGTATAGA-TCTTGATTGAAAAATAAA-TATTTGTCC

UNTRANSF         CAACTCTCTTTTATYCC-TGTGTCCATGTCTGAACAACTYT
                 **************** ***********************

T227-1 left    CAACTCTCTTTTATTCCCTGTGTCCATGTCTGAACAACTTT

UNTRANSF         CGAATTTTCTTCCTAATAATCTCGCGATAACTTGCATGGTT
                 *****************************************

T227-1 left    CGAATTTTCTTCCTAATAATCTCGCGATAACTTGCATGGTT

UNTRANSF         TGGAACATGCAATGAGCGAGAAATAGAAATTTTATTTCTGC
                 *****************************************

T227-1 left    TGGAACATGCAATGAGCGAGAAATANAAATTTTATTTCTGC

UNTRANSF         TTTGAAAGCAATTGTTAGAATGCATCGTCSTACWGTGATTG
                 *****************************************

T227-1 left    TTTGAAAGCAATTGTTAGAATGCATCGTCCTACTGTGATTG

UNTRANSF         CATGAGTGGAAACACATATGGGAGGAAATCAASCTATGTCT
                 *****************************************

T227-1 left    CATGAGTGGAAACACATATGGGAGGAAATCAAGCTATGTCT

UNTRANSF         ATTGCATCTGCTCTGGGGTACTCTGGTCATACTCGTGTCGA
                 *****************************************

T227-1 left    ATTGCATCTGCTCTGGGGTACTCTGGTCATACTCGTGTCGA

UNTRANSF         TGCCATGGGTTTTTTAGGGGGAATTTTGATWTATTGGAAAC
                 *****************************************

T227-1 left    TGCCATGGGTTTTTTAGGGGGAATTTTGATTTATTGGAAAC
```

FIGURE 8 CONTINUED

| | |
|---|---|
| UNTRANSF | CAGAATTGGKWRCCATAGAACCTATCATTAGACATGCATGA |
| T227-1 left | CAGAATTGGTTACCATAGAACCTATCATTAGACATGCATGA |

| | |
|---|---|
| UNTRANSF | TCAACATATAACCATGGAAATAAAAAGGGTWGGGGCTATTC |
| T227-1 left | TCAACATATAACCATGGAAATAAAAAGGGTAGGGGCTATTC |

| | |
|---|---|
| UNTRANSF | CTTTGGTATTTCTCAGCGGTTTATGCGAGTCCSGACCCTAC |
| T227-1 left | -TTTGGTATTTCTCAGCGGTTTATGCGAGTCCCGACCCTAC |

| | |
|---|---|
| UNTRANSF | AWAACGCCAAGTTACTTTGGCAAGAATTAAGAAATTTCGCT |
| T227-1 left | AAAACGCCAAGTT-CTTTGGCAAGAATTAAGAAATTTCGCT |

| | |
|---|---|
| UNTRANSF | CGAACTCATWMTCAMGCTKSGCTCATRGCMSGAGAWTTTAA |
| T227-1 left | CGAACTCATAATCAAGCTTGGCTCATAGCAGGAGATTTTAA |

| | |
|---|---|
| UNTRANSF | TGWK-CCARATKBCCTATGAAAGGAAA |
| T227-1 left | TGATACCAGATATTCCTATGAAAGGAATACTGCTTGTTCGG |

FIGURE 9 Restriction sites of the enzymes on pMON17227.
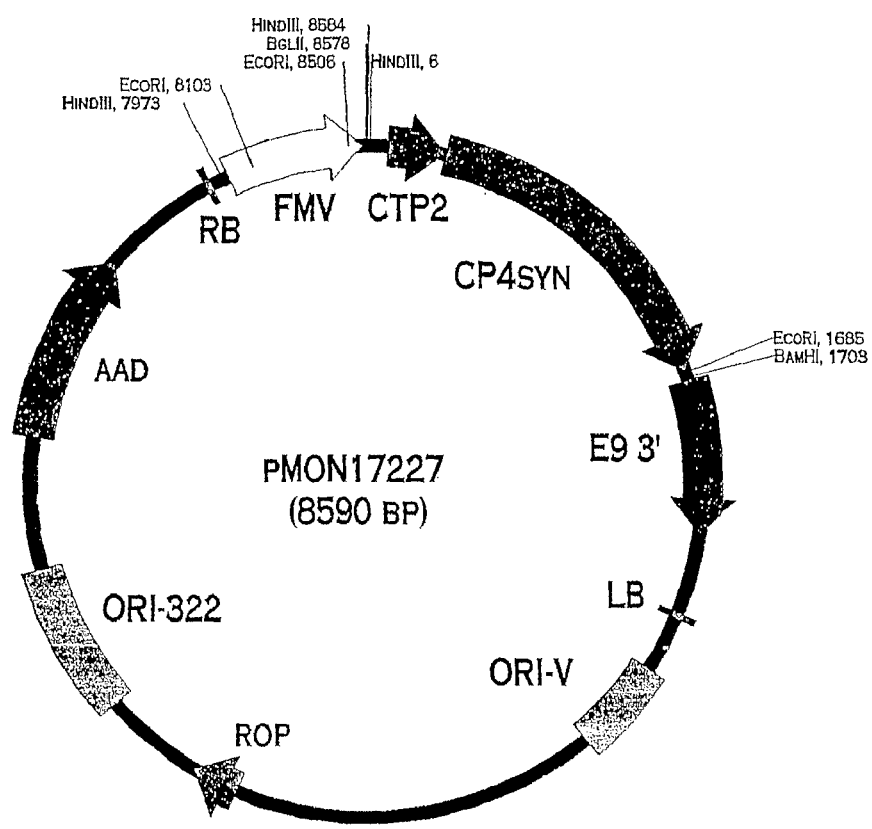

Figure 10a

Sequence of the right border fragment obtained with the 98K89 – RB12 primer set.

98K89 primer
AGAACCCACC TCATCTTAAA CCAAACTAAA ATATCATTTA ATACATATCC  50
AAGTCATAAT CTACTAGTAG TTTTGCTTGG TGAGATTACA TAATATATCA  100
CTAATATATA AGAAATTTAT TTTTCAATCA AGATCTATAC AACTAATAAC  150
TGAAGTAGGA GAAGATATGG GATTGGTGTG GGAGATGGCT TCATGTCCAT  200
GTGTTTATTC CCATCAAGCT TGAGCTCAGG ATTTAGCAGC ATTCCA  246
                                        RB12 primer

Figure 10b

Sequence of the right border fragment obtained with the 98K89 – 98I50 primer set.

98K89 primer
AGAACCCACC TCATCTTAAA CCAAACTAAA ATATCATTTA ATACATATCC  50
AAGTCATAAT CTACTAGTAG TTTTGCTTGG TGAGATTACA TAATATATCA  100
CTAATATATA AGAAATTTAT TTTTCAATCA AGATCTATAC AACTAATAAC  150
TGAAGTAGGA GAAGATATGG GATTGGTGTG GGAGATGGCT TCATGTCCAT  200
GTGTTTATTC CCATCAAGCT TGAGCTCAGG ATTTAGCAGC ATTCCAGATT  250
GGGTTCAATC AACAAGGTAC GAGCCATATC ACTTTATTCA AATTGGTATC  300
GCCAAAACCA AGAAGGAACT CCCATCCTCA AAGGTTTGTA AGGAAGAATT  350
CTCAGTCCAA AGCCTCAACA AGGTCAGGGT ACAGAGTCTC CAAACCATTA  400
GCCAAAAGCT ACAGGAGATC AATGAAGAAT CTTCAATCAA AGTAAACTAC  450
TGTTCCAGCA CATGCATCAT GGTCAG
         98I50 primer

Figure 10c

Sequence of the left border fragment obtained with the 98G94 – 98K86 primer set.

```
        98G94 primer
CGCCTATAAA TACGACGGAT CGTAATTTGT CGTTTTATCA AAATGTACTT   50
TCATTTTATA ATAACGCTGC GGACATCTAC ATTTTTGAAT TGAAAAAAAA  100
TTGGTAATTA CTCTTTCTTT TTCTCCATAT TGACCATCAT ACTCATTGCT  150
GATCCATGTA GATTTCCCGG ACATGAAGCC ATTTCCCATA TCTTCTCCTA  200
CTTCNAGTCN ATTAGTTGTA TAGATCTTGA TTGAAAAATA AATATTTGTC  250
CCAACTCTCT TTTATTCCCT GTGTCCATGT CTGAACAACT TTCGAATTTT  300
CTTCCTAATA ATCTCGCGAT AACTTGCATG GTTTGGAACA TGCAATGAGC  350
GAGAAATANA AATTTTATTT CTGCTTTGAA AGCAATTGTT AGAATGCATC  400
GTCCTACGTG ATTGCATGAG TGGAAACACA TATGGGAGGA AATCAAGCTA  450
TGTCTATTGC ATCTGCTCTG GGGTACTCTG GTCATACTCG TGTCGATGCC  500
ATGGGTTTTT TAGGGGGAAT TTTGATTTAT TGGAAACAGA ATTGGTTACC  550
ATAGAACCTA TCATTAGACA TGCATGATCA ACATATAACC ATGGAAATAA  600
AAAGGGTAGG GGCTATTCTT TGGTATTTCT CAGCGGTTTA TGCGAGTCCC  650
GACCCTACAA AACGCCAAGT TCTTTGGCAA GAATTAAGAA ATTTCGCTCG  700
AACTCATAAT CAAGCTTGGC TCATAGCAGG AGATTTTAAT GATACCAGAT  750
ATTCCTATGA AAGGAATACT GCTTGTTCGG AAACTCAACG TT          792
                              98K86 primer
```

US 7,645,579 B2

T227-1 FLANKING SEQUENCE

FIELD OF THE INVENTION

The field of the invention broadly covers a herbicide resistant transformed sugar beet that is detectable by the specific primers developed to match the DNA sequences that flank the left and/or right border region of the inserted transgenic DNA and the method of identifying primer pairs containing plant genomic DNA/plasmid DNA. More specifically the present invention covers a specific glyphosate resistant sugar beet plant having an insertion of the transgenic material identified as the T227-1 event. The present invention additionally covers primer pairs: plant genomic DNA/Plasmid DNA that are herein identified. Additionally, these primer pairs for either the left or the right flanking regions make an event specific test for the T227-1 insert of transgenic material. These event specific tests using the primers include a method that employs electrophoresis through gels as the standard method used to separate, identify and purify DNA fragments. The location of the DNA that are separated by size within the gels can be determined by using a dye. This dye permits DNA bands with 1-10 ng of DNA to be detected under ultraviolet light.

BACKGROUND

In the last few years there has been numerous commercial products having glyphosate resistance plants such as soybeans, maize, and rapeseed. At least two different genes have been used to make these commercial products. These products have had a specific event which has been developed through extensive research and testing and then registered with the regulatory authorities in the various countries as genetically modified organisms.

The regulatory requirements in Europe for introduction of plants that have had foreign DNA introduced are most stringent. Although not a specific requirement regulatory offices favor inserted events containing DNA which is necessary for the expression of the introduced trait and very little extra DNA in the insert. On the practical side, the event should have low numbers of copies to avoid problems with gene silencing. Development of these types of insertion events in certain crops such as sugar beets can be difficult. The inserted event should provide the plant with the desired levels of gene expression such as resistance to the application of a herbicide, resistance to insect attack, or production of an oil or sugar, and the like.

Additionally, there is the need to have an insert in sugar beet that is identifiable through tests developed for the inserted event. These test results can be employed to track the GMO in production plants and fields.

There is a need to be able to clearly identify a transgenic plant through its inserted DNA. The need for identifiable transgenic events and the primers and the event specific tests for these primers are increasingly evident.

SUMMARY OF THE INVENTION

Broadly the present invention is to a method of detecting a glyphosate resistant sugar beet comprising the steps of forming primers that flank the genomic and plasmid sequence border in the sugar beet which can uniquely identify the sugar beet, by using a PCR to sequence the unique fragment produced by the primers and detecting the absence or presence of the fragment. The present invention covers a glyphosate resistant sugar beet detectable by this method. Additionally this invention covers a transgenic glyphosate resistant sugar beet comprising an insertion of DNA unique to T227-1 and its progeny. This invention is detectable by either of the pair of primers for the left or right border. The primer set capable of generating a DNA fragment unique to identify T227-1 of 50 base pairs and more preferably approximately 100 base pairs. Wherein the DNA fragment unique to identify T227-1 includes some base pairs related to the sugarbeet genomic DNA and some base pairs related to the inserted plasmid DNA (from pMon 17227) in T227-1. A sugar beet that is detectable with a pair of primers in accordance with the present invention that border the left flanking sequence identified as 98G94 and 98K86 generating a 792 bp fragment.

A sugar beet is also detectable with the pair of primers that border the right flanking sequence identified as 98I50 and 98K89 generating a 476 bp fragment. Or the primer set 98K89-RB12 can also be employed to produce a unique fragment of 246 base pairs.

The invention also includes the pairs of primers comprising DNA which flank at least one of the border regions of the insertion of DNA into the T227-1 Event.

The T 227-1 event is sugarbeet material that is capable of glyphosate resistance when in the plant form and is capable of being detected by at least one of the pair of primers 98G94 and 98K86, 98I50 and 98K89, and/or 98K89-RB12. The primers should when a positive result is produced identify a DNA fragment of the length associated with that set of primers, negative results should give non DNA fragment or a fragment of a length not associated with the primers. The invention has identified a pair of primers comprising DNA which lies in right border region of insertion of DNA into the T227-1 Event wherein one primer lies in the plant genomic material and the other primer is in the inserted plasmid material.

The invention has also identified a pair of primers comprising DNA which lies in the left border region (FIG. 6) of insertion of DNA into the T227-1 Event wherein one primer lies in the plant genomic material and the other primer is in the inserted plasmid material.

The primers themselves are generated to identify the T227-1 event by employing a PCR test using a pair of primers. The primers are used in a PCR method to detect the presence or absence of the T227-1 event. A test kit for the T227-1 event can be formed with the primers as components thereof.

The method of detecting the T227-1 event including the steps of selecting sugar beet genomic material for testing; employing at least one of the pair of primers capable of detecting the T227-1 event in association with such selected material; and using a PCR machine to amplify the DNA fragment if it exists; detecting the presence or the absence of the DNA fragment.

The transgenic glyphosate resistant sugar beet of the present invention is characterized by an unique sequence of DNA having at least 80% homology to the right border sequence in FIG. 3 or the left border sequence in FIG. 6 comprising genomic sugar beet DNA proximate the breakpoint of the insertion of the DNA into the genome and inserted plasmid DNA.

This invention encompasses a transgenic glyphosate resistant sugar beet wherein at least a 10-20 base pair fragment of said sequence of DNA is capable of detection by a pair of flanking primers wherein one of said primers is developed from the genomic sugar beet DNA proximate the breakpoint of the insertion of the DNA into the genome and one of said primers being developed from the inserted DNA plasmid.

BRIEF DESCRIPTION OF THE FIGURES

FIG. 4 shows the sequence of the right border breakpoint.

FIG. 5 shows the alignment of the right breakpoint region in the transformed sugarbeet T227-1 with the untransformed plant allelic sequence.

FIG. 7 shows the sequence of the left border breakpoint between the sugar beet genomic material and the inserted plasmid material.

FIG. 8 shows the alignment of the left breakpoint region and the untransformed plant allelic sequence.

FIG. 9 shows the plasmid pMON17227.

FIG. 10a shows the sequence of the right border fragment obtained with the 98K89-RB12 primer set.

FIG. 10b shows the sequence of the right border fragment obtained with the 98K89-98I50 primer set.

FIG. 10c shows the sequence of the left border fragment obtained with the 98G94-98K86 primer set.

DETAILED DESCRIPTION OF THE INVENTION

Figure 1:
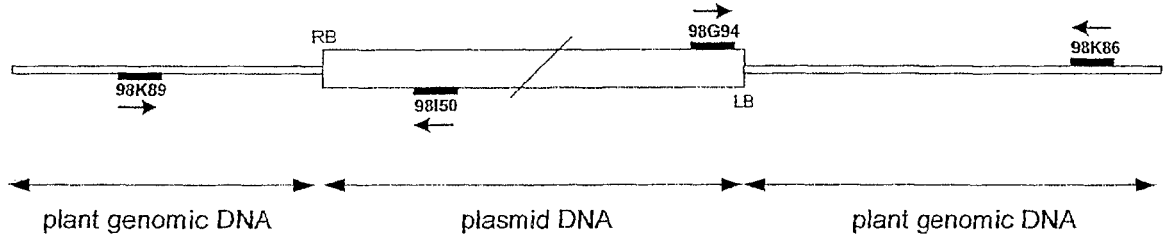
FIG. 1 shows the primers used in the flanking PCR test.

The selection of a specific event in sugar beets (*Beta vulgaris*) requires the production of numerous transformants. These transformants must be screened in most instances to eliminate those transformants that do not conform fairly closely with the genotype of the original germplasm employed. These transformants must be tested for the efficiency of the inserted event. On a molecular basis these transformants must be tested for copy number to mostly to select for low copy number which may avoid gene silencing. Additionally, the transformants are tested and developed and screened based on the positional effect the location in the genome the inserted event has on the gene activity. Different insertion sites in the genome results in different overall results. For example, if the insertion is located in an area with high transcription there may be many copies of the protein produced; if the insertion is located in an area with low transcription, the protein may not be produced at sufficient levels for the desired gene effect. Thus, the selection of an insertion in recalcitrant plant such as sugar beet involves numerous levels of investigative work and research. This type of research and development differs from plant to plant, from gene to gene, and according to the desired results.

The present invention broadly encompasses a sugar beet which is resistant to glyphosate at levels that would normally result in the death of the sugar beet plant. The resistance has been introduced by the *Agrobacterium* mediated transformation of the sugar beet with the pMON17227 plasmid This plasmid is shown in FIG. 9 and it contains the FMV 35S promoter. The 35 S promoter is from a modified figwort mosaic virus. It also contains the chloroplast transit peptide from the EPSPS gene of *Arabidopsis*. And the CP4 synthetic gene optimized from the 5-enolpyruvylshikimate-3-phosphate synthase (CP4 EPSPS) gene from *Agrobacterium* sp. Strain CP4. This plasmid also contains the terminator from pea. The terminator is from the pea gene RBCSE9. The E9 3' is the pea rbcS (small subunit ribulose bisphosphate carboxylase oxygenase) E9 gene. The plasmid also includes the left and right T-DNA border sequences from *Agrobacterium*.

Numerous transformants were produced by the *Agrobacterium* mediated transformation of the sugar beet. The plantlets that survived the initial transformation stages were then screened in a green house for herbicide resistance. Levels of differing doses of herbicide were applied to the plant to determine which transformants were sensitive and which were resistant. The sensitive transformants were destroyed by the herbicide application and the resistant plants were subjected to further analysis based on comparison to the genome of the original germplasm employed in the transformation process. The transformants that were not eliminated in this screening were further selected from in further green house experiments. The resulting selected transgenic plants were analysed on a different criteria including on the molecular level.

This analysis led to the selection of a rare event insertion designated T227-1. The transformation method used to generate T227-1 integrated the vector into the genome by breakage of the circular vector at a position that was relative to the left and right border sequences. In the *Agrobacterium* system, the left and right border sequences are specifically recognised by vir genes (virD1 and virD2). These proteins produce nicks in the border sequences and the fragment is transferred from the bacterial cell into the plant cell as a single stranded T-DNA molecule, not as a circular vector.

To characterise T227-1 fully, as well as providing information that could serve as a basis for event-specific PCR tests, the nucleotide sequence of the breakpoints between inserted vector and plant genomic DNA was determined.

Flanking Sequences T227-1

Genomic sequences flanking the T227-1 insert were isolated by linker PCR. Genomic DNA was digested with restriction endonucleases and linkers attached to the ends of the fragments obtained. The fragments containing the T227-1 sequences were preferentially amplified by PCR using the linker sequence and pMON 17227-specific sequences as primers The PCR products were sequenced directly, and the sequences used to design further primers, which were used to amplify plant genomic DNA from T227-1 and from untransformed plants.

Genomic plant DNA fragments were isolated for both left and right borders. These linker PCR products were sequenced and these sequences were aligned with (a) pMON17227 and (b) the fragments generated by the plant genomic primers using plant DNAs (containing the transformed and untransformed "alleles") as templates.

Although the sequence contains some ambiguities, these are essentially consistent with the sequences being identical.

Right Breakpoint

Figure 3:
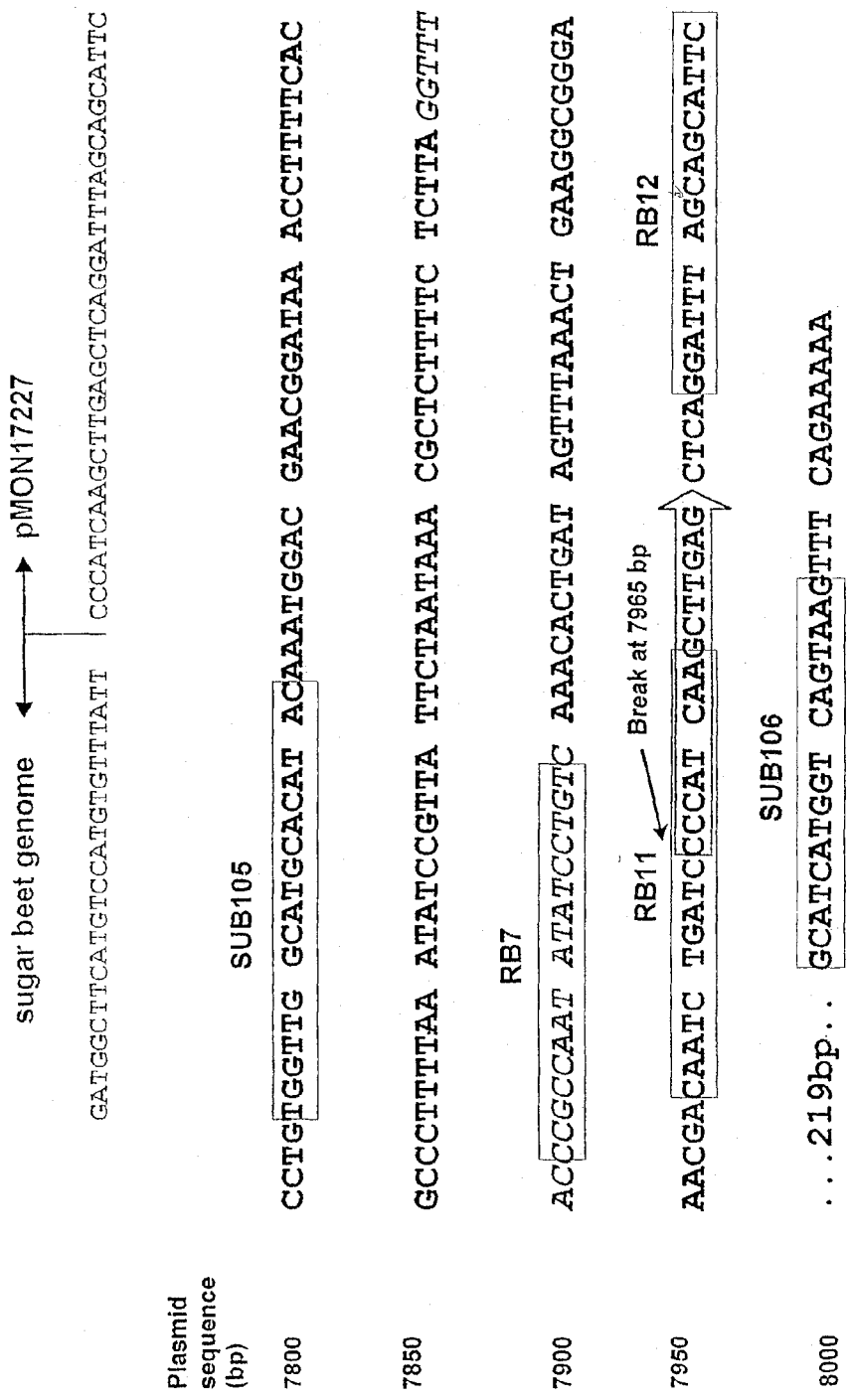
FIG. 3 shows the plasmid sequence at the right border.

The present invention has its sugar beet genetic makeup at the insert sites in the right and left border regions identified and defined. In FIG. 3 the plasmid sequence at the right border is shown. The inserted DNA sequence was from pMON17227. The top portion of the drawing shows the sequence of the right border of the insert, the sugar beet genome and the beginning of the inserted foreign DNA. The Sub 105, the RB7 and the RB11 are small primer regions. The various combinations of primer regions can be employed singly or in pairs. The break at 7965 base pairs (indicated by the arrow) shows where the insertion has occurred. The DNA before this break is genomic sugar beet and after the break is the sequence from the plasmid.

FIG. 4 shows the sequence of the right border breakpoint and where the primers lie on this sequence. In the fourth row of sequence data the bolded sequence indicates the DNA sequence of the 98K89 primer. The bolded sequence in the sixth line of sequence indicates the restriction site of BglII. The sequence that is in the greyed in area is the beginning of the integrated plasmid material from pMON17227. Within the greyed area are two separate bolded portions of sequence. The first bolded sequence portion is the HindIII restriction site. The second bolded sequence portion is the RB12 primer sequence. The pair of primers, when employed allow the PCR fragment of DNA that is also unique to this event to be generated.

FIG. 5 shows the alignment of the right breakpoint region in the transformed sugar beet T227-1 with the untransformed plant allelic sequence. The sequence matches up so that it shows that the gene in the untransformed plant and the T227-1 event match. Certain base pairs could not be identified as ACTG and the following classification was used as listed in Table 1.

TABLE 1

| |
|---|
| S = G or C |
| R = A or G |
| W = A or T |
| K = G or T |
| M = A or C |
| Y = C or T |
| N = any base |
| B = C, G or T |

There is a 17 base pair fragment in the last line of the sequence before the start of the plasmid sequence that indicates that there are 17 base pairs in the T227-1 transformed sugar beet that differs from the untransformed. After this 17 base pair fragment, which is in italics, the plasmid sequence data is found.

The alignments of sequence data at the right side of the integration site are shown in FIG. 5. The nucleotides common to both the transformant (T227-1) and the plasmid (pMON17227) are indicated by an asterisk (*) below the aligned sequence.

Between the vector breakpoint and the beginning of homology with beet genomic sequences, a 17 bp fragment is found which is not present in the untransformed allelic sequences studied in this germplasm. No perfect homology could be found between this short unknown DNA sequence and the plasmid sequence.

These results are entirely consistent with the Southern and PCR analyses of T227-1.

Left Breakpoint

Figure 6:
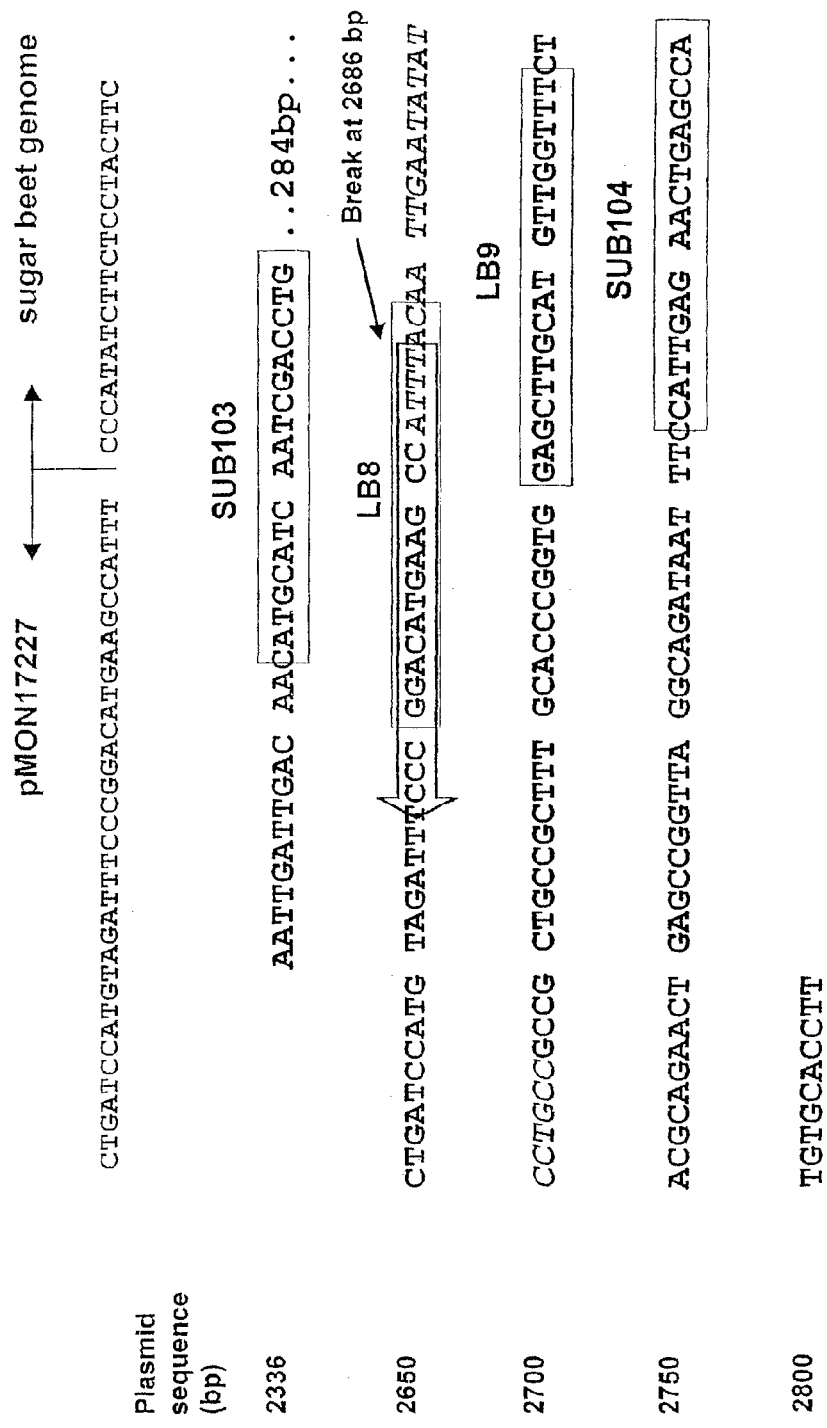
FIG. 6 shows the plasmid sequence at the left border.

FIG. 6 shows the plasmid sequence at the left border. The inserted DNA sequence was from pMON17227. The top portion of the drawing shows the sequence of the left border of the insert and the associated sugar beet genome. The base pair 2336 is a portion of the left border of the inserted DNA material. The Sub 103, Sub 104, LB8 and the LB9 are small primer regions. The break at 2686 base pairs (indicated by the arrow) shows where the insert border has occurred. The DNA before this break is the sequence from the plasmid and after the break is genomic sugar beet.

FIG. 7 shows the sequence of the left border breakpoint between the sugar beet genomic material and the inserted plasmid material. The greyed in region is the integrated plasmid sequence. At the end of this sequence is the bolded primer LB8. In the next line is the bolded sequence that indicates the restriction site for BglII. The primer that is located in the sugar beet genomic material is identified in bold in the figure at the bottom.

FIG. 8 shows the alignment of the left breakpoint region and the untransformed plant allelic sequence. The T227-1 transformed event starts with the plasmid sequence. Then there is a region of sparse matching between the untransformed and the T227-1, a fragment of 49 base pairs. Thereafter there is a close correlation between the untransformed sugar beet and the transformed sugar beet called event T227-1.

The alignments of sequences from the left side of the integration site and its known component elements are shown in FIG. 8.

At the 3' end of the sequence there is clear homology to the pMON 17227 vector though there is a 49 base pair fragment that sparsely aligns with the untransformed beet "allele", or to pMON17227.

On the basis of the sequence shared by the transformant and the plasmid it is clear that a 4 base pair section of the left T-DNA border was incorporated into the Event T227-1 during or following the transformation event. No right T-DNA border and very little of the left T-DNA border portions, were integrated into the transgenic sugar beet event entitled T227-1.

Beyond this 4 base pair section of the left T-DNA border region from *Agrobacterium* the plasmid sequence has been entirely integrated, excluding the right border section of the *Agrobacterium* region, after which point recombination has taken place to insert the construct into the beet genome.

These results are fully consistent with the Southern hybridisation results.

Use of Flanking Primers to Analyse T227-1 and Untransformed Sugar Beet

Specific primers were developed from the left and right flanking sequences, and used in PCR reactions with each other or individually with primers from within the insert. Primer locations in the inserted DNA and in the sequence flanking the insert are shown in FIGS. 1, 3-7 and Table 1.

PCR reactions between a flanking primer and an insert primer always gave the size expected from the sequence information, and have never given any product in untransformed beet or transformants other than T227-1. Thus these sequences are used as an event-specific test whereby the T227-1 event is identified. This identification process of the insertion of event T227-1 which is one copy and has little extraneous DNA and is highly efficacious at resisting the effects of glyphosate on the plant, is possible in the original germplasm and in progeny developed by any manner of breeding or selfing. The material from the progeny including pollen and seeds and the like can be tested for the presence of this insert in the DNA.

Genomic Flanking Sequences

The plasmid shown in FIG. 9 contained the LB (left border) RB (the right border), the FMV 35S promoter (from a modified figwort mosaic virus), and the main gene of interest to give glyphosate resistance the CP4 syn: the 5-enolpyruvylshikimate-3-phosphate synthase (CP4 EPSPS) gene from *Agrobacterium* sp. Strain CP4. The plasmid also contains a chloroplast transit peptide and a terminator from pea. The circular vector pMON17227 opens at both left and right borders when inserted into the plant genome to form the transformed Event. The selected transformation event was the T227-1 Event. This transformed beet T227-1 and its progeny show excellent levels of glyphosate tolerance.

To characterize T227-1 fully, providing information that serves as a basis for event-specific PCR tests, the nucleotide sequences of the breakpoints between inserted vector and plant genomic DNA were determined.

Genomic sequences flanking the T227-1 insert were isolated by linker PCR. Genomic DNA was digested with restriction endonucleases and linkers attached to the ends of the fragments obtained. The fragments containing the T227-1 sequences were preferentially amplified by PCR using the linker sequence and pMON17227-specific sequences as primers. The PCR products were sequenced directly, and the sequences used to design further primers; these were then used to amplify plant genomic DNA from the T227-1 transformant for both left and right borders (flanking sequences PCR) and from an untransformed plant.

FIG. 1 shows the primers used in the flanking PCR test. The first pair of primers is in the light border region of the inserted material. 98k89 is a primer that is located within the sugar beet plant genome. 98I50 is a primer that is located in the inserted plasmid DNA sequence. In combination these primers can be employed to produce a unique piece of DNA through a PCR test. This unique DNA specifically identifies this T227-1 transformation event. The sugar beet identified by this PCR flanking sequence is only the T227-1 event or its progeny.

The second pair of primers is in the left border region of the inserted material. 98K86 is a primer that is located within the sugar beet plant genome. 98G94 is a primer that is located in the inserted plasmid DNA sequence. In combination these primers can be employed to produce a unique piece of DNA through a PCR test. These event specific tests using the primers include a method that employs electrophoresis through gels as the standard method used to separate, identify and purify DNA fragments. The location of the DNA that is separated by size within the gels can be determined by using a dye. This dye permits DNA bands with 1-10 ng of DNA to be detected under ultraviolet light. This unique DNA specifically identifies this T227-1 transformation event. The sugar beet identified by this PCR flanking sequence is only the T227-1 event or its progeny. Test kits comprising at least one set of primers wherein one such primer is located within the sugar beet plant genome proximate the insert and the other such primer is located within the inserted plasmid DNA sequence of T227-1, wherein an unique piece of DNA is capable of being identified wherein the material is identified as being GMO positive or GMO negative. Additionally the material can be more specifically identified as being T227-1 or its progeny.

Primers 98K89 and 98K86 for the T227-1 event or its progeny are situated in the regions flanking the inserted sequences, while 98I50 and 98G94 lie inside the DNA from the vector. The resulting PCR products are described in Table 2.

TABLE 2

Specific primers inside and outside the integrated vector sequence.

| | Vector specific primer (position) | Flanking DNA primer | PCR product |
|---|---|---|---|
| Left border | 98G94 (2503 bp) | 98K86 | 792 bp |
| Right border | 98I50 (8232 bp) | 98K89 | 476 bp |

PCR with these primers was performed on a 9600 thermocycler from PE-Biosystems. In each 50 µl reaction, 50 ng of plant DNA was incubated with 120 ng of each primer and 1 U of Amplitaq DNA Polymerase in GeneAmp PCR buffer II containing 10 mM Tris-HCl pH8.3 and 50 mM KCl complemented with 1.5 mM $MgCl_2$ and 0.2 mM dNTP. One PCR reaction consisted of a hot start of 3 min. at 94° C. followed by 35 cycles (one cycle: 30 sec. at 94° C., 1 min. at 57° C. and 1 min, at 72° C.) The PCR products were separated on a 1.5% agarose gel.

This amplification clearly demonstrates that the left and right flanking sequences are normally contiguous in sugar beet, and have not suffered major reorganisation as a result of the transformation.

Flanking Sequences—Progeny of T227-1

By sequencing the flanking regions we developed specific primers from the left and right flanking sequences, and used these in PCR reactions with each other or individually with primers from within the insert. Such a PCR assay can be used to identify the T227-1 transformation event and its progeny uniquely.

Primer pairs (plant genomic DNA/plasmid DNA) for both the left and the right region were tested on T227-1, its progeny and the non-transformed lines. Both primer combinations gave positive results for all the glyphosate resistant plants (all generations). All these PCR products were identical to those obtained with transformation event T227-1. The fragment lengths of a few of the combinations are listed in FIGS. 10a-10c. Other primer pairs can give different fragments. The glyphosate sensitive plants and the non-transformed line, however, showed no amplification product at all.

Figure 2:
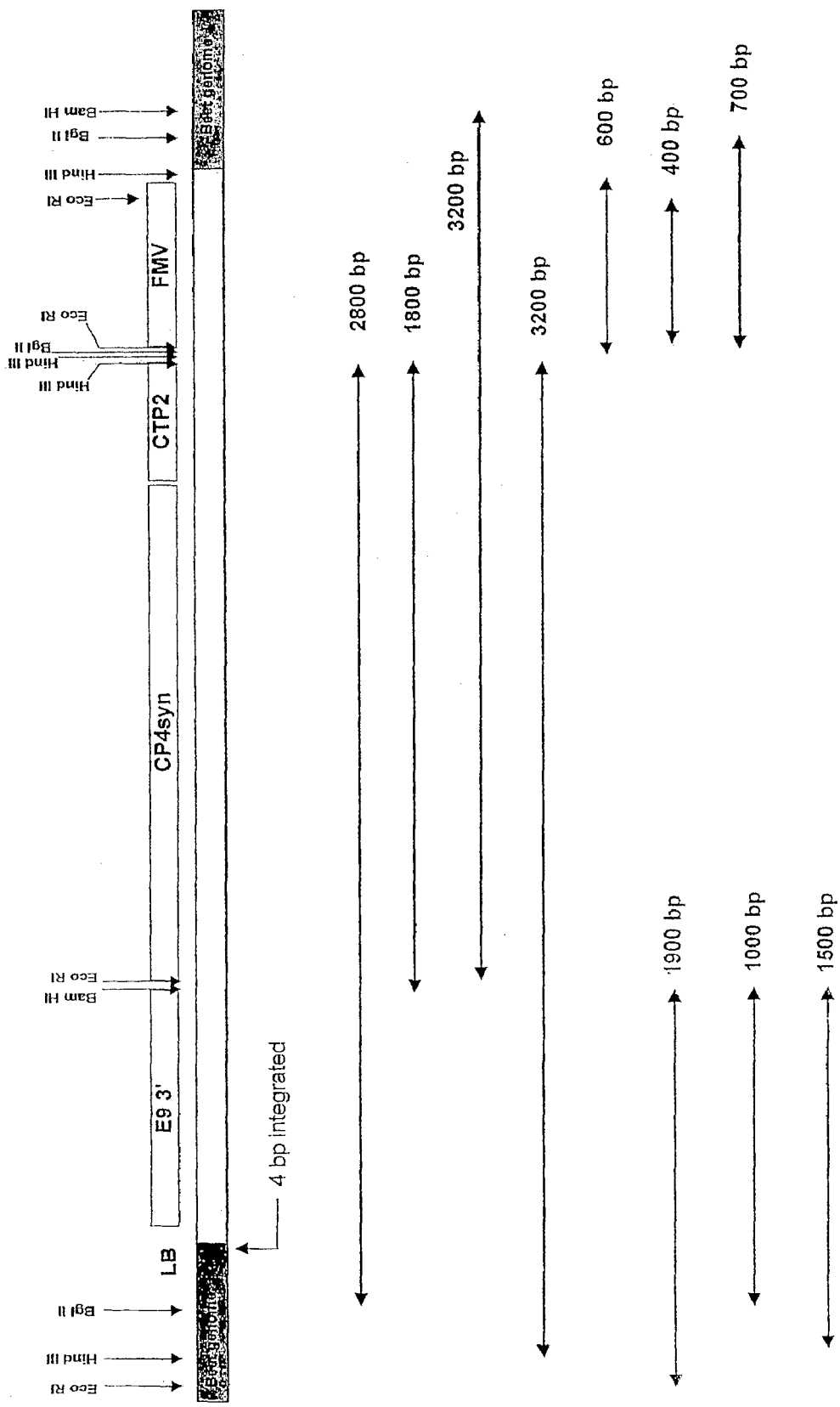
FIG. 2 shows the diagrammatic interpretation of the Southern blot results.

The T227-1 event and its progeny were tested for this unique DNA by using Southern blots. FIG. 2 shows the diagrammatic interpretation of the Southern blot results. The four boxes on top of the figure depict the plasmid sequence DNA that was incorporated into the transformed sugar beet T227-1. The components of the plasmid differ somewhat from the inserted material. The sugar beet was transformed through the use of *Agrobacterium*. Therefore, the plasmid contained both the right and left T-DNA border regions. The right T-DNA border sequence was not transformed into T227-1. The left T-DNA border sequence was not transformed except for a small 4 base pair section that is integrated between the sugar beet plant genome and the E9 3' terminator sequence.

The inserted material is identified as FMV, CTP 2, CP4 syn, E9 3', LB. FVM is a 35S promoter from a modified figwort mosaic virus. CP4 syn is the 5-enolpyruvylshikimate-3-phosphate synthase (CP4 EPSPS) gene from *Agrobacterium* sp. Strain CP4. CTP2 is the chloroplast transit peptide from *Arabidopsis*. E9 3' is the terminator. LB is the small portion of the left border sequence from *Agrobacterium*.

The vertical arrows depict the restriction sites located in the genome and the inserted material. The horizontal lines below the top two boxes depict the approximate number of base pairs that are in a fragment that is produced by employing the restriction enzyme indicated on the top box. The second box depicts the transformed sugar beets genetic makeup at the insert site.

The beet genomic sequences flanking this insert have been sequenced, and employed to design specific PCR tests for the T227-1 insertion. Flanking primers may be used for amplification of untransformed sugar beet DNA, indicating that the transformation did not induce any major rearrangements in the beet genome. This is confirmed by sequence analysis, which shows that the sequences on either side of the insert are essentially collinear with those of untransformed "alleles"

from the same locus. Thus the present invention includes a method of using primers that identify T227-1 in a PCR method of detecting DNA. The invention also covers each of the two pair of primers that flank the right and left borders. The invention further covers the sugar beet having the DNA that is detectable by the primers.

The embodiments of the invention in which an exclusive property or privilege is claimed are follows:

1. A transgenic glyphosate resistant sugar beet comprising a transgenic insert of DNA having a 5' end and 3' end, the insert of DNA comprising a figwort mosaic virus 35s promoter, DNA encoding a chloroplast transit peptide from the EPSPS gene of *Arabidopsis*, an optimized CP4 EPSPS gene from *Agrobaclerium* sp. strain CP4, and a terminator, wherein said insert of DNA is detectable by a pair of primers, selected from the group consisting of:

the pair of primers identified as 98G94 consisting of nucleotides 1-20 of SEQ ID NO: 15 and 98K86 consisting of nucleotides 730-753 of SEQ ID NO: 10; and the pair of primers identified as 98I50 consisting of nucleotides 455-476 of SEQ ID NO: 14 and 98K89 consisting of nucleotides 155-180 of SEQ ID NO: 4.

2. A sugar beet according to claim 1 that is detectable with the pair of primers identified as 98G94 consisting of nucleotides 1-20 of SEQ ID NO: 15 and 98K86 consisting of nucleotides 730-753 of SEQ ID NO: 10.

3. A sugar beet according to claim 1 that is detectable with the pair of primers identified as 98I50 consisting of nucleotides 455-476 of SEQ ID NO: 14 and 98K89 consisting of nucleotides 155-180 of SEQ ID NO: 4.

4. A sugar beet according to claim 1 that is detectable with the pair of primers identified as 98K89 consisting of nucleotides 155-180 of SEQ ID NO: 4 and RB12 consisting of nucleotides 185-200 of SEQ ID NO: 2.

5. A sugar beet according to claim 1 that is detectable with the pair of primers that produce a nucleotide sequence consisting of SEQ ID NO: 13, SEQ ID NO: 14 or SEQ ID NO: 15.

* * * * *

SEQUENCE LISTING

```
<160> NUMBER OF SEQ ID NOS: 15

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Plasmid
      sequence at the right border

<400> SEQUENCE: 1
gatggcttca tgtccatgtg tttattccca tcaagcttga gctcaggatt tagcagcatt    60
c                                                                    61

<210> SEQ ID NO 2
<211> LENGTH: 200
<212> TYPE: DNA
<213> ORGANISM: Artificial Sequence
<220> FEATURE:
<223> OTHER INFORMATION: Description of Artificial Sequence: Plasmid
      sequence at the right border

<400> SEQUENCE: 2
cctgtggttg gcatgcacat acaaatggac gaacggataa accttttcac gcccttttaa    60
atatccgtta ttctaataaa cgctcttttc tcttaggtta acccgccaat atatcctgtc   120
aaacactgat agtttaaact gaaggcggga aacgacaatc tgatccccat caagcttgag   180
ctcaggattt agcagcattc                                               200

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Plasmid
      sequence at the right border

<400> SEQUENCE: 3
gcatcatggt cagtaagttt cagaaaaa                                       28

<210> SEQ ID NO 4
<211> LENGTH: 400
<212> TYPE: DNA
<213> ORGANISM: Artificial Sequence
<220> FEATURE:
<223> OTHER INFORMATION: Description of Artificial Sequence: Sequence of
      the right border breakpoint

<400> SEQUENCE: 4
ggacaggaca cgacagctcc tcacgaggta atggatatca ttagagaaag agcggaacaa    60
atattactca aatggaggat ttatgaaagt aatagatata ctttactaga aaggaagat    120 tgtcatgatt caacaccaaa tgacacttaa attaagaacc cacctcatct taaaccaaac   180
taaaatatca tttaatacat atccaagtca taatctacta gtagttttgc ttggtgagat   240
tacataatat atcactaata tataagaaat ttatttttca atcaagatct atacaactaa   300
taactgaagt aggagaagat atgggattgg tgtgggagat ggcttcatgt ccatgtgttt   360
```
attcccatca agcttgagct caggatttag cagcattcca                             400

<210> SEQ ID NO 5
<211> LENGTH: 192
<212> TYPE: DNA
<213> ORGANISM: Beta vulgaris

<400> SEQUENCE: 5
atttaaatrt cwkttgmcac atatccaagt cataatctac kasyagttttk gcttggtgag     60 attacataat akatcactaa tatataasaa atttatttwt caatcaagat ctatacaact    120
aatwmctgaa gtaggagaag atatgggatt ggtgtgggas atggattccc catataaagt    180
aaagagagtc aa                                                        192

<210> SEQ ID NO 6
<211> LENGTH: 240
<212> TYPE: DNA
<213> ORGANISM: Artificial Sequence
<220> FEATURE:
<223> OTHER INFORMATION: Description of Artificial Sequence: Transformed
      sugar beet T227-1

<400> SEQUENCE: 6
aattaagaac ccacctcatc ttaaaccaaa ctaaaatatc atttaataca tatccaagtc     60
ataatctact agtagttttg cttggtgaga ttacataata tatcactaat atataagaaa    120 tttattttc aatcaagatc tatacaacta ataactgaag taggagaaga tatgggattg    180
gtgtgggaga tggcttcatg tccatgtgtt tattcccatc aagcttgagc tcaggattta    240

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence: Plasmid
      sequence at the left border

<400> SEQUENCE: 7
ctgatccatg tagatttccc ggacatgaag ccatttccca tatcttctcc tacttc         56

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Plasmid
      sequence at the left border

<400> SEQUENCE: 8
aattgattga caacatgcat caatcgacct g                                    31

<210> SEQ ID NO 9
<211> LENGTH: 160
<212> TYPE: DNA
<213> ORGANISM: Artificial Sequence
<220> FEATURE:
<223> OTHER INFORMATION: Description of Artificial Sequence: Plasmid
      sequence at the left border

<400> SEQUENCE: 9
ctgatccatg tagatttccc ggacatgaag ccatttacaa ttgaatatat cctgccgccg     60
ctgccgcttt gcaccggtg gagcttgcat gttggtttct acgcagaact gagccggtta    120
ggcagataat ttccattgag aactgagcca tgtgcacctt                          160

<210> SEQ ID NO 10
<211> LENGTH: 797
<212> TYPE: DNA
<213> ORGANISM: Artificial Sequence
<220> FEATURE:
<223> OTHER INFORMATION: Description of Artificial Sequence: Sequence of the left border breakpoint
<220> FEATURE:
<221> NAME/KEY: misc_feature
<222> LOCATION: 6, 21, 53, 90, 108, 136, 164, 169, 318, 778..780
<223> OTHER INFORMATION: n = any base

<400> SEQUENCE: 10

```
aatgtncttt cattttataa naacgctgcg gacatctaca tttttgaatt ganaaaaaat      60
tggtaattac tctttctttt tctccatatn gaccatcata ctcattgntg atccatgtag     120
atttcccgga catgangcca tttcccatat cttctcctac ttcnagtcna ttagttgtat     180
agatcttgat tgaaaaataa atatttgtcc caactctctt ttattccctg tgtccatgtc     240
tgaacaactt tcgaattttc ttcctaataa tctcgcgata acttgcatgg tttggaacat     300
gcaatgagcg agaaatanaa attttatttc tgctttgaaa gcaattgtta gaatgcatcg     360
tcctactgtg attgcatgag tggaaacaca tatgggagga aatcaagcta tgtctattgc     420
atctgctctg gggtactctg gtcatactcg tgtcgatgcc atgggttttt tagggggaat     480
tttgatttat tggaaaccag aattggttac catagaacct atcattagac atgcatgatc     540
aacatataac catggaaata aaagggtag gggctattct ttggtatttc tcagcggttt     600
atgcgagtcc cgaccctaca aaacgccaag ttctttggca agaattaaga aatttcgctc     660
gaactcataa tcaagcttgg ctcatagcag gagattttaa tgataccaga tattcctatg     720
aaaggaatac tgcttgttcg gaaactcaac gttgtctctt agtttcaatg attgggtnnn    780
tgacatggat taatgaa                                                   797
```

<210> SEQ ID NO 11
<211> LENGTH: 593
<212> TYPE: DNA
<213> ORGANISM: Beta vulgaris

<400> SEQUENCE: 11

```
atatgggatt ggtgtgggas atggattccc catataaagt aaagagagtc aacaagaaga      60
wataaaatat ttgtcccaac tctcttttat yccctgtgtcc atgtctgaac aactytcgaa    120
ttttcttcct aataatctcg cgataacttg catggtttgg aacatgcaat gagcgagaaa    180
tagaaatttt atttctgctt tgaaagcaat tgttagaatg catcgtcsta cwgtgattgc    240
atgagtggaa acacatatgg gaggaaatca asctatgtct attgcatctg ctctggggta    300
ctctggtcat actcgtgtcg atgccatggg ttttttaggg ggaattttga twtattggaa    360
accagaattg gkwrccatag aacctatcat tagacatgca tgatcaacat ataaccatgg    420
aaataaaaag ggtwggggct attcctttgg tatttctcag cggtttatgc gagtccsgac    480
cctacawaac gccaagttac tttggcaaga attaagaaat tcgctcgaa ctcatwmtca    540
mgctksgctc atrgcmsgag awtttaatgw kccaratkbc ctatgaaagg aaa            593
```

<210> SEQ ID NO 12
<211> LENGTH: 607
<212> TYPE: DNA
<213> ORGANISM: Artificial Sequence
<220> FEATURE:
<223> OTHER INFORMATION: Description of Artificial Sequence: Transformed

```
        sugar beet T227-1
<220> FEATURE:
<221> NAME/KEY: misc_feature
<222> LOCATION: 30, 35, 184
<223> OTHER INFORMATION: n = any base

<400> SEQUENCE: 12
aagccatttc ccatatcttc tcctacttcn agtcnattag ttgtatagat cttgattgaa      60
aaataaatat ttgtcccaac tctctttat tccctgtgtc catgtctgaa caactttcga     120
attttcttcc taataatctc gcgataactt gcatggtttg gaacatgcaa tgagcgagaa    180 atanaattt tatttctgct ttgaaagcaa ttgttagaat gcatcgtcct actgtgattg     240
catgagtgga aacacatatg ggaggaaatc aagctatgtc tattgcatct gctctggggt    300
actctggtca tactcgtgtc gatgccatgg gttttttagg gggaattttg atttattgga    360
aaccagaatt ggttaccata gaacctatca ttagacatgc atgatcaaca tataaccatg    420
gaaataaaaa gggtaggggc tattctttgg tatttctcag cggtttatgc gagtcccgac    480
cctacaaaac gccaagttct ttggcaagaa ttaagaaatt cgctcgaac  tcataatcaa    540 gcttggctca tagcaggaga ttttaatgat accagatatt cctatgaaag gaatactgct    600
tgttcgg                                                              607

<210> SEQ ID NO 13
<211> LENGTH: 246
<212> TYPE: DNA
<213> ORGANISM: Artificial Sequence
<220> FEATURE:
<223> OTHER INFORMATION: Description of Artificial Sequence: Sequence of
      the right border fragment obtained with the 98K89
      - RB12 primer set

<400> SEQUENCE: 13
agaacccacc tcatcttaaa ccaaactaaa atatcattta atacatatcc aagtcataat     60
ctactagtag ttttgcttgg tgagattaca taatatatca ctaatatata agaaatttat    120
ttttcaatca agatctatac aactaataac tgaagtagga gaagatatgg gattggtgtg    180
ggagatggct tcatgtccat gtgtttattc ccatcaagct tgagctcagg atttagcagc    240
attcca                                                               246

<210> SEQ ID NO 14
<211> LENGTH: 476
<212> TYPE: DNA
<213> ORGANISM: Artificial Sequence
<220> FEATURE:
<223> OTHER INFORMATION: Description of Artificial Sequence: Sequence of
      the right border fragment obtained with the 98K89
      - 98I50 primer set

<400> SEQUENCE: 14
agaacccacc tcatcttaaa ccaaactaaa atatcattta atacatatcc aagtcataat     60
ctactagtag ttttgcttgg tgagattaca taatatatca ctaatatata agaaatttat    120
ttttcaatca agatctatac aactaataac tgaagtagga gaagatatgg gattggtgtg    180
ggagatggct tcatgtccat gtgtttattc ccatcaagct tgagctcagg atttagcagc    240
attccagatt gggttcaatc aacaaggtac gagccatatc actttattca aattggtatc    300
gccaaaacca agaaggaact cccatcctca aaggtttgta aggaagaatt ctcagtccaa    360
agcctcaaca aggtcagggt acagagtctc caaaccatta gccaaaagct acaggagatc    420
aatgaagaat cttcaatcaa agtaaactac tgttccagca catgcatcat ggtcag        476
```

```
<210> SEQ ID NO 15
<211> LENGTH: 792
<212> TYPE: DNA
<213> ORGANISM: Artificial Sequence
<220> FEATURE:
<223> OTHER INFORMATION: Description of Artificial Sequence: Sequence of
      the left border fragment obtained with the 98G94 -
      98K86 primer set
<220> FEATURE:
<221> NAME/KEY: misc_feature
<222> LOCATION: 205, 210, 359
<223> OTHER INFORMATION: n = any base

<400> SEQUENCE: 15
cgcctataaa tacgacggat cgtaatttgt cgttttatca aaatgtactt tcattttata      60
ataacgctgc ggacatctac attttttgaat tgaaaaaaaa ttggtaatta ctctttcttt    120
ttctccatat tgaccatcat actcattgct gatccatgta gatttcccgg acatgaagcc    180
atttcccata tcttctccta cttcnagtcn attagttgta tagatcttga ttgaaaaata    240
aatatttgtc ccaactctct tttattccct gtgtccatgt ctgaacaact ttcgaatttt    300
cttcctaata atctcgcgat aacttgcatg gtttggaaca tgcaatgagc gagaaatana    360
aattttattt ctgctttgaa agcaattgtt agaatgcatc gtcctacgtg attgcatgag    420
tggaaacaca tatgggagga aatcaagcta tgtctattgc atctgctctg gggtactctg    480
gtcatactcg tgtcgatgcc atgggttttt taggggggaat tttgatttat tggaaacaga    540
attggttacc atagaaccta tcattagaca tgcatgatca acatataacc atggaaataa    600
aaagggtagg ggctattctt tggtatttct cagcggttta tgcgagtccc gaccctacaa    660
aacgccaagt tctttggcaa gaattaagaa atttcgctcg aactcataat caagcttggc    720
tcatagcagg agattttaat gataccagat attcctatga aaggaatact gcttgttcgg    780
aaactcaacg tt                                                         792
```